US006916658B2

(12) United States Patent  
Li et al.

(10) Patent No.: US 6,916,658 B2  
(45) Date of Patent: *Jul. 12, 2005

(54) METHOD FOR MEASUREMENT OF IMMATURE GRANULOCYTES

(75) Inventors: Jing Li, Miami, FL (US); Yi Li, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/770,193

(22) Filed: Feb. 2, 2004

(65) Prior Publication Data

US 2004/0171164 A1 Sep. 2, 2004

Related U.S. Application Data

(63) Continuation-in-part of application No. 10/702,352, filed on Nov. 6, 2003, now abandoned, which is a continuation of application No. 10/226,800, filed on Aug. 23, 2002, now Pat. No. 6,673,618, which is a continuation-in-part of application No. 10/165,699, filed on Jun. 7, 2002, now abandoned, which is a continuation of application No. 09/917,533, filed on Jul. 27, 2001, now Pat. No. 6,410,330.

(51) Int. Cl.[7] .......................... G01N 31/00; G01N 33/48
(52) U.S. Cl. .................... 436/10; 436/8; 436/17; 436/63; 436/149; 436/150; 422/73; 422/82.01; 422/82.02; 435/2; 435/29; 435/34; 435/39
(58) Field of Search .................. 436/8, 10, 17, 436/18, 63, 149, 150; 422/73, 82.01, 82.02; 435/2, 4, 29, 34, 39

(56) References Cited

U.S. PATENT DOCUMENTS 2,656,508 A 10/1953 Coulter
3,810,011 A 5/1974 Coulter et al.
5,125,737 A 6/1992 Rodriguez et al.
5,242,832 A 9/1993 Sakata
5,298,426 A 3/1994 Inami et al.
5,413,938 A * 5/1995 Tsujino et al. ................. 436/63
5,538,893 A * 7/1996 Sakata et al. ................... 436/10
5,559,037 A 9/1996 Kim et al.
5,648,225 A 7/1997 Kim et al.
5,763,280 A 6/1998 Li et al.
5,843,608 A 12/1998 Li et al.
5,874,310 A 2/1999 Li et al.
5,879,900 A 3/1999 Kim et al.
5,882,934 A 3/1999 Li et al.
5,917,584 A 6/1999 Li et al.
6,246,786 B1 * 6/2001 Nishikiori et al. ............ 382/134
6,410,330 B1 6/2002 Li et al.
6,472,215 B1 10/2002 Huo et al.
6,514,763 B2 2/2003 Carver et al.
6,573,102 B2 6/2003 Li et al.
6,653,063 B2 11/2003 Carver et al.
6,653,137 B2 11/2003 Ryan
6,673,618 B1 * 1/2004 Li et al. ........................ 436/10
6,723,563 B2 4/2004 Ryan
2005/0002826 A1 1/2005 Oguni et al.

FOREIGN PATENT DOCUMENTS

EP 1004880 A2 5/2000
WO WO 95/24651 9/1995

* cited by examiner

Primary Examiner—Maureen M. Wallenhorst
(74) Attorney, Agent, or Firm—Cuspa Technology Law Associates; Mitchell E. Alter

(57) ABSTRACT

A method for measuring immature granulocytes in a blood sample is described. The method includes the steps of lysing red blood cells of a blood sample with a lytic reagent, analyzing the sample mixture by DC impedance measurement, determining immature granulocytes from obtained DC histogram, and reporting immature granulocytes in the blood sample. The method further includes measuring nucleated red blood cells in the blood sample.

11 Claims, 3 Drawing Sheets

METHOD FOR MEASUREMENT OF IMMATURE GRANULOCYTES

CROSS-REFERENCE TO RELATED APPLICATION

This application is a continuation-in-part of application Ser. No. 10/702,352, filed Nov. 6, 2003, now abandoned, which is a continuation of application Ser. No. 10/228,800, filed on Aug. 23, 2002, now U.S. Pat. No. 6,673,618, which is a continuation-in-part of application Ser. No. 10/165,699, filed on Jun. 7, 2002, now abandoned, which is a continuation of application Ser. No. 09/917,533, filed on Jul. 27, 2001, now U.S. Pat. No. 6,410,330. All prior applications are incorporated herein by reference in their entireties.

FIELD OF THE INVENTION

The present invention relates to a method for determination of immature granulocytes in a blood sample. More specifically the method determines immature granulocytes using a direct current impedance measurement.

BACKGROUND OF THE INVENTION

The presence of immature granulocytes (IG) in peripheral blood is potentially important information which indicates enhanced bone marrow activation. Besides the obvious significance of blasts for the diagnosis of leukaemia, the promyelocyte, myelocyte and metamyelocyte stages of myeloid maturation may indicate systemic inflammatory stress or leukaemic reactions. The determination of immature granulocytes is routinely done by visual microscopy, which requires manual review of each blood sample smear, and is a labor intensive and time consuming task.

Currently, several high end hematology analyzers which utilize optical, fluorescence and impedance measurements to provide automated determination of immature granulocytes of the blood samples. However, these instruments and their detection systems are expensive, and not suitable for low cost analyzers. Therefore, there is a need for automated and inexpensive determination of immature granulocytes and reduction of manual review rate.

On the other hand, the presence of nucleated red blood cells (NRBCs), or referred to as erythroblasts, one type of immature red blood cells, in the peripheral blood is also important information for diagnosis of certain diseases, such as anemia, and leukemia, etc. Therefore, it is of clinical importance to measure nucleated red blood cells in blood samples. Traditionally, differentiation and enumeration of NRBC are performed manually. The process involves the smearing of a blood sample on a microscope slide and staining the slide, followed by manual visual analysis of the individual slide. The NRBC concentration is reported as numbers of NRBC per 100 white blood cells. Usually, 200 white blood cells and the numbers of NRBC present in the same region on a blood smear are counted and the numbers are divided by 2 to express the NRBC concentration as the numbers of NRBC/100 WBC. This approach is time-consuming as well as being subjective to the interpretation of the individual analyzing the slide.

In recent years, several fluorescence flow cytometry methods have been developed for differentiating NRBCs. These methods utilizes specific nuclear staining technique to distinguish NRBCs from other cell types because it is difficult to differentiate NRBCs based on their electronic or optical properties.

U.S. Pat. No. 6,410,330 (to Li et al) discloses a method for differentiation of nucleated red blood cells. The method includes the steps of lysing red blood cells of a blood sample with a lytic reagent, measuring nucleated blood cells by DC impedance measurement in a non-focused flow aperture, differentiating nucleated red blood cells from other cell types, and reporting nucleated red blood cells in the blood sample.

U.S. Pat. No. 6,472,215 (to Huo et al) teaches a method of differentiating nucleated red blood cells by lysing a first aliquot and a second aliquot of a blood sample separately with a first lysing reagent system and a second lysing reagent system; measuring the first sample mixture in a flow cell by DC impedance, radio frequency, and light scatter measurements; measuring cell distributions and counting remaining blood cells in the second sample mixture by DC impedance measurements in a non-focused flow aperture; analyzing blood cell distribution patterns obtained from measuring the first sample mixture and from measuring the second sample mixture respectively; and further performing a combined analysis to differentiate NRBCs from other cell types and determine numbers of NRBCs in the blood sample.

Furthermore, a well known problem with NRBC containing samples is erroneous white blood cell count (WBC) reported by hematology analyzers on these samples. Since the nuclear volumes of NRBC are close to those of white blood cells, and they are commonly counted as white blood cells on hematology analyzers which measure the sizes of blood cells, resulting an elevation of WBC. Therefore, correction of NRBC contribution to the WBC reported from hematology analyzer is required for samples containing NRBC. Current practice in the clinical laboratory is to subtract the numbers of NRBC obtained by manual count from the WBC count reported by the hematology analyzers. This is time consuming and error prone.

Based on foregoing, there exists a need for a simple and less costly analysis method for differentiating and enumerating nucleated red blood cells. Furthermore, it is desirable to provide automated determination of immature granulocytes together with the determination of nucleated red blood cells in one concurrent test.

SUMMARY OF THE INVENTION

In one embodiment, the present invention is directed to a method of measuring immature granulocytes. The method comprises steps of mixing a blood sample with a lytic reagent to lyse red blood cells, and to form a blood sample mixture; analyzing the blood sample mixture by a DC impedance measurement, and obtaining a blood cell distribution of the blood sample mixture from the DC impedance measurement; determining immature granulocytes from the obtained blood cell distribution; and reporting immature granulocytes in the blood sample. The immature granulocytes referred herein comprise myelocytes, promyelocytes, metamyelocytes, myeloblasts and promyeloblasts.

In a further embodiment, the present invention is directed to a method concurrently measuring immature granulocytes and nucleated red blood cells. The method comprises the steps of: mixing a blood sample with a lytic reagent to lyse red blood cells, and to form a blood sample mixture; analyzing the blood sample mixture by a DC impedance measurement and obtaining a blood cell distribution from the DC impedance measurement; determining nucleated red blood cells and immature granulocytes from the obtained blood cell distribution; and reporting nucleated red blood cells and immature granulocytes in the blood sample. The DC impedance measurement can be performed using non-focused flow aperture or focused flow cell. The non-focused flow aperture has an aperture aspect ratio of 0.7 and greater.

The present invention provides a cost effective method using DC impedance measurement for measuring immature granulocytes, as well as concurrently, measuring nucleated red blood cells of a blood sample.

DETAILED DESCRIPTION OF THE INVENTION

In one embodiment, the present invention provides a method of measuring immature granulocytes (IG). More specifically the method measures immature granulocytes in a blood sample by a direct current (DC) impedance measurement.

The immature granulocytes referred herein include myelocytes, promyelocytes, metamyelocytes, myeloblasts and promyeloblasts.

In one specific embodiment, the method comprises the steps of mixing a blood sample with a lytic reagent to lyse red blood cells, and to form a blood sample mixture; analyzing the blood sample mixture by a DC impedance measurement, and obtaining a blood cell distribution histogram of the blood sample mixture; determining immature granulocytes from the obtained blood cell distribution; and reporting immature granulocytes in the blood sample.

To lyse a blood sample, the blood sample can be diluted first by a blood diluent, then mixed with a sufficient amount of a lytic reagent to lyse red blood cells. For the purpose of the present invention, the blood diluent contains a sufficient amount of salt or salts for impedance measurement of the sample mixture. Suitable examples of salts are alkaline metal salts.

A blood diluent is commonly used on an automated hematology analyzer to dilute a blood sample for measuring red blood cells, where the blood diluent is adjusted to isotonic by salts for maintaining the blood cell volumes. It is convenient to use commercially available isotonic blood diluents for the purpose of the present invention, although isotonicity is not required for the measurement of immature granulocytes.

The lytic reagent compositions suitable to use with a blood diluent for the present invention have been described in U.S. Pat. Nos. 6,410,330 and 6,573,102, which are hereby incorporated by reference in their entirety. Alternatively, a lytic reagent further containing a sufficient amount of a salt or salts for impedance measurement can be used for lysing a blood sample without a separate blood diluent. Suitable examples of salts are alkaline metal salts, such as sulfates, chlorides, phosphates, and citrates.

The measurement of immature granulocytes can be performed using DC impedance measurement in a non-focused flow aperture, or a focused flow cell. When a particle, such as a blood cell, passes through the aperture, an electrical signal can be measured due to conductivity or impedance change. The pulse shape, height and width, is directly related to the size of a particle, and can be converted to the size of the particles measured. When two or more particles of different sizes are measured, the histogram obtained from the measurement can represent size distribution of the particles.

The detection methods used for blood cell counting and sizing by a blood analyzer equipped with a DC impedance measurement device are generally described in U.S. Pat. No. 2,656,508 (to Coulter), and U.S. Pat. No. 3,810,011 (to Coulter, et al), which are hereby incorporated by reference in their entirety.

Figure 1A:
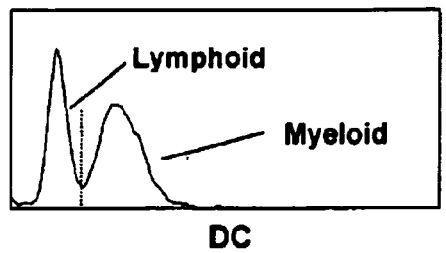
FIG. 1A shows a DC histogram of a normal blood sample analyzed according to the procedure described in Example 1.

Example 1 illustrates an exemplary process for measurement of immature granulocytes using DC impedance measurement. FIG. 1A shows a DC histogram of a normal blood sample analyzed according to the procedure described in Example 1. As shown for a normal blood sample, the white blood cells had a bi-module distribution, with the lymphoid subpopulation on the left and the myeloid subpopulation on the right. No cell population located on the right side of the myeloid subpopulations.

Figure 1B:
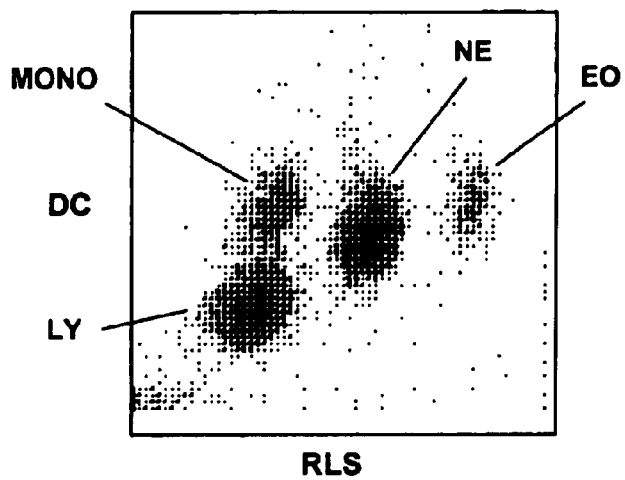
FIG. 1B shows a VCS scattergram of the same blood sample shown in FIG. 1A, analyzed according to the procedure described in Example 1.

FIG. 1B shows a VCS scattergram of the same blood sample shown in FIG. 1A, analyzed according to the procedure described in Example 1. The term of VCS denotes a three-dimensional measurement technology which measures the direct current (DC) and radio frequency (RF) impedances, and light scatter signals of a blood cell when it passes through a flow cell. The details of VCS technology are described in U.S. Pat. No. 5,125,737, which is hereby incorporated by reference in its entirety. As shown for a normal blood sample, the white blood cells are differentiated into four subpopulations in this two-dimensional, i.e., DC vs RLS scattergram. No cell population located in the area above the neutrophils. It is noted that RLS is an abbreviation of the term "rotated light scatter" which is defined as a function of a medium angle light scatter signal and DC impedance signal.

Figure 2A:
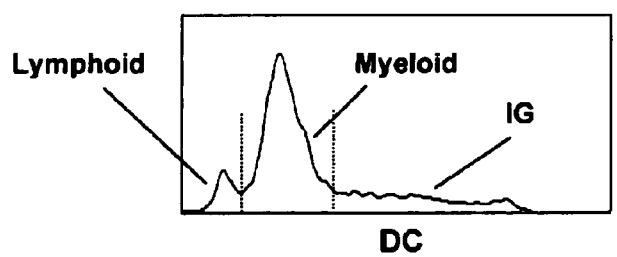
FIG. 2A shows a DC histogram of a clinical sample containing immature granulocytes analyzed according to the procedure described in Example 1.

FIG. 2A shows a DC histogram of a clinical sample containing immature granulocytes analyzed according to the procedure described in Example 1. The manual reference reported about 25% of immature granulocytes, including metamyelocytes, myelocytes and promyelocytes. As shown, there were substantial amount of cells located on the right side of the myeloid subpopulation.

Figure 2B:
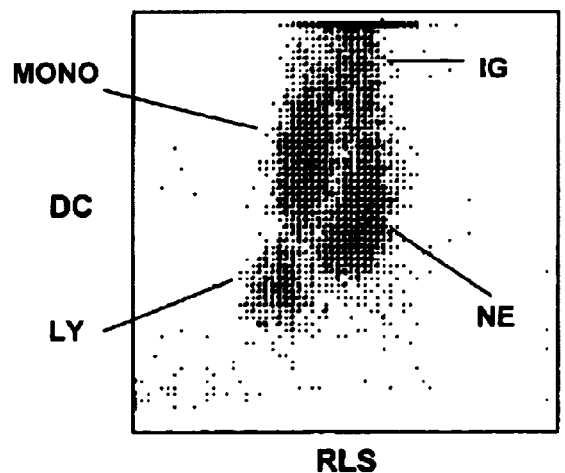
FIG. 2B shows a VCS scattergram of the same blood sample shown in FIG. 2A, analyzed according to the procedure described in Example 1.

FIG. 2B shows a VCS scattergram of the same clinical blood sample shown in FIG. 2A, analyzed according to the procedure described in Example 1. As shown, there were substantial amount of cells located in the area above the neutrophils. This is the area where immature granulocytes typically show in the VCS scattergram and that has been utilized for detecting the presence of immature granulocytes using the VCS technology.

Figure 3A:
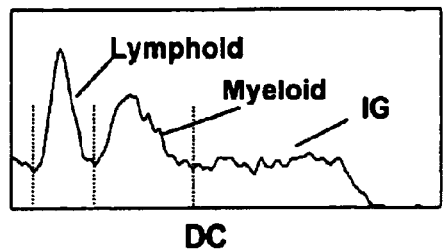
FIGS. 3A and 3B show a DC histogram and a VCS scattergram respectively, of a normal sample with addition of promyelocytes produced by cell line in vitro, as described in Example 2.
Figure 3B:
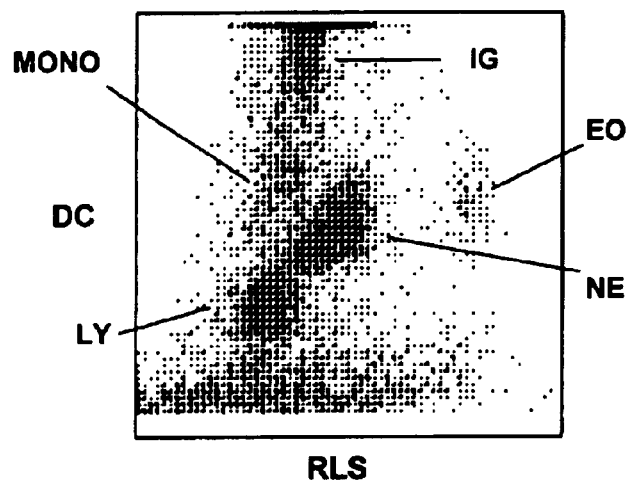

Example 2 illustrates the identification of immature granulocytes using the DC impedance measurement described above. As described in Example 2, a first test blood sample was prepared by adding a predetermined amount of promyelocytes produced by cell line in vitro into the normal whole blood sample shown in FIGS. 1A and 1B. FIG. 3A shows the DC histogram of the first test blood sample, analyzed according to the procedure described in Example 1. As shown, a substantial amount of cells located on the right side of the myeloid subpopulation, similar to that shown in FIG. 2A. FIG. 3B shows a VCS scattergram of the first test blood sample shown in FIG. 3A. It is apparent that the promyelocytes located above the monocytes and neutrophils. It is noted that for the purpose of identification of the immature granulocytes, an abnormally large amount of the promyelocytes was added in the whole blood sample. The addition caused increased amount debris of the sample in the histogram and scattergram and impact on the integrity of the neutrophils.

Figure 4A:
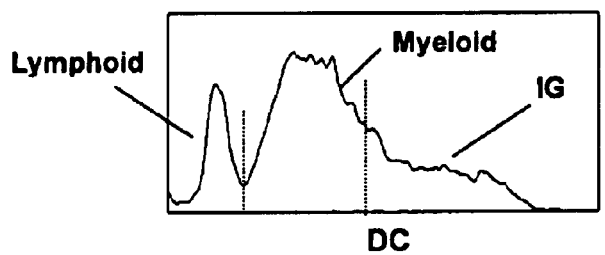
FIGS. 4A and 4B show a DC histogram and a VCS scattergram respectively, of a normal sample with addition of promyeloblasts produced by cell line in vitro, as described in Example 2.
Figure 4B:
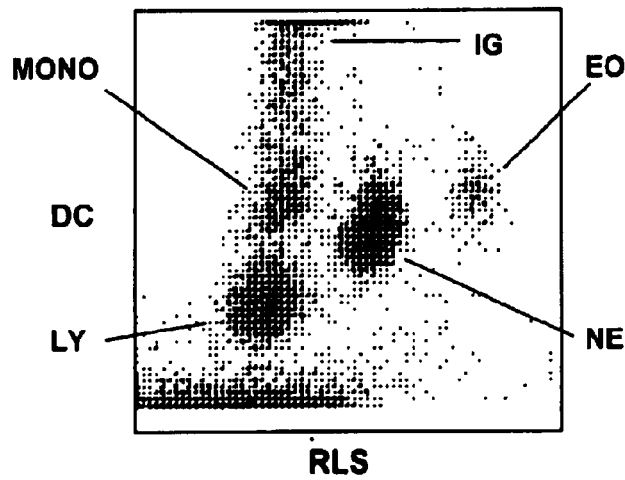

A second test blood sample was prepared by adding a predetermined amount of promyeblasts produced by cell line in vitro into the normal whole blood sample shown in FIGS. 1A and 1B. FIG. 4A shows the DC histogram of the second test blood sample, analyzed according to the procedure described in Example 1. As shown, a substantial amount of cells located on the right side of the myeloid subpopulation. FIG. 4B shows a VCS scattergram of the second test blood sample shown in FIG. 4A. It is apparent that the promyeloblasts located above the monocytes.

These two test samples clearly illustrated the distribution characteristics of the two immature granulocytes on the DC histograms, which positively identified the cells of the clinical sample shown in FIG. 2A as immature granulocytes, which was consistent with the manual reference report.

In a further embodiment, the present invention provides a method of concurrently measuring immature granulocytes and nucleated red blood cells. The sample preparation, the reagents and the DC measurement of the sample mixtures have been described above. In the presence of nucleated red blood cells, the obtained blood cell distribution histogram can be used for determining both immature granulocytes and nucleated red blood cells in the blood sample.

The method of measuring nucleated red blood cells using DC impedance measurement has been described in U.S. Pat. No. 6,410,330, which is hereby incorporated by reference in its entirety. More specifically, it is found that the aperture aspect ratio, defined as a ratio of the aperture length versus the aperture width, affects the separation of different sizes of blood cells, in particular for the cell populations which have relatively narrow distributions, such as in the situation of separating nucleated red blood cells from lymphocytes. With the method of the present invention, separation of the NRBC population from the other cell types can be achieved by using an aperture aspect ratio of 0.7 and greater.

It has been understood that aperture aspect ratio affects the flow profile of a flow passing through the aperture, which in turn, affects trajectory of particles in the flow. In general, with a fixed aperture width, the rate of a flow at the center of the flow increases with increasing the length of the aperture. Therefore, with an increase of the aperture aspect ratio, a flow rate gradient, from the sides of the flow which interface with the wall of aperture toward center of the flow, increases. In the presence of such a flow rate gradient, particles suspended in a flow passing through the aperture tend to move to the center of the flow. Therefore, under such a condition, particles have a similar behavior to the particles passing through a focused flow aperture. A focused flow aperture can be used in the present invention for measuring nucleated blood cells, particularly for differentiating blood cells having similar sizes. However, the cost of a focused flow aperture is much higher than a non-focused flow aperture.

On the other hand, it is known that at a cross section of an aperture, an imposed electrical field has a different strength along the cross section. Consequently, the particles passing through a non-focused flow aperture can generate various pulse shapes because each particle may experience a different electrical field depending on its position along the cross section of the aperture. These pulse distortions cause distortion of the particle size distribution in the measured histogram. Historically, pulse editing has been broadly used in the art to edit out seriously distorted pulses, and improve particle size differentiation to a certain degree. It is understood that with increase of the aperture aspect ratio, electrical field gradient along the cross section, from the center to the side wall of the aperture, decreases. Consequently, electrical pulses generated from the particles not passing the center of the aperture have less distortions because of the presence of a more homogeneous electrical field along the cross section.

Therefore, with an increase of aperture aspect ratio the two effects, control of particle trajectory in the non-focused flow aperture and reduction of electrical field gradient along the cross section of the aperture, improve ability of differentiation of different sizes of particles.

It has been found using a non-focused flow aperture with an aperture aspect ratio of 0.7 and greater, the NRBC population can be differentiated from closely sized other nucleated blood cells, particularly lymphocytes. Preferably, an aperture aspect ratio of 1.0 and greater is used. More preferably, an aperture aspect ratio about 1.2 is used.

To further increase the aperture aspect ratio, the separation of NRBC from other cell types can be further improved. However, when the aperture aspect ratio is 1.5 or above, the throughput of the sample mixture passing through the aperture for measurement reduces significantly, and it can render the measurement incompatible to the throughput requirement of a hematology instrument. Therefore, it should be understood that an aperture aspect ratio about 1.2 is selected based on a balance between the population separation and throughput of the measurement for a practical reason. Theoretically, an aperture aspect ratio above 1.2 can be used for separating the NRBCs from other cell types.

Figure 5A:
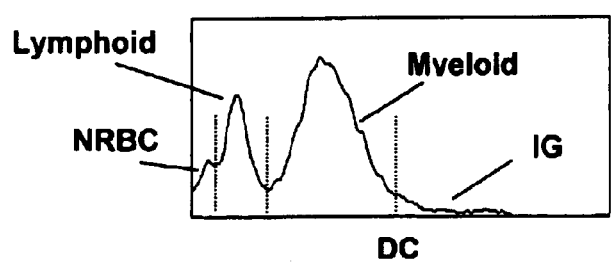
FIGS. 5A and 5B show a DC histogram and a VCS scattergram respectively, of a clinical blood sample containing immature granulocytes and nucleated red blood cells, as described in Example 3.
Figure 5B:
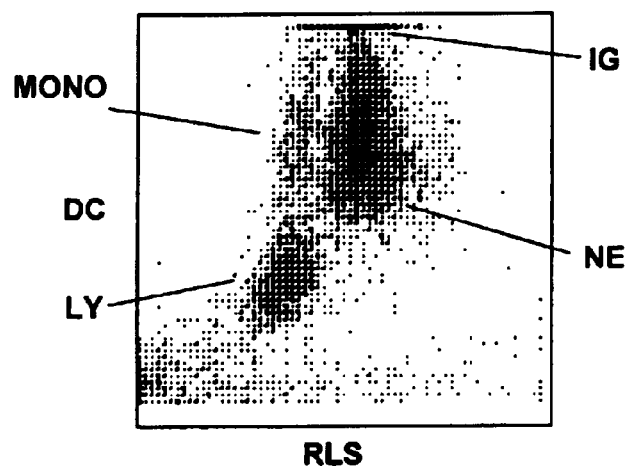

FIG. 5A shows a DC histogram of a clinical blood sample containing 10% NRBCs and 10% of immature granulocytes analyzed using the procedure described in Example 1, as described in Example 3. As shown, the NRBC population located at the most left of the histogram, and the immature granulocytes extending on the right side of the myeloid population. It is noted that these two types of immature cells have very different distribution characteristics. NRBCs appeared in a narrow peak, while the immature granulocytes spread out in a large area of the histogram, hence had flat appearance. FIG. 5B shows a VCS scattergram of the same clinical blood sample shown in FIG. 5A. As can be seen, a small amount of large cells appeared along the top of the scattergram, which was consistent with the cell distribution pattern on the DC histogram shown in FIG. 5A.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

A whole blood sample was aspirated by an experimental hematology analyzer. A first aliquot of 28 $\mu l$ was diluted with 6 ml of Coulter® LH Series Diluent (Beckman Coulter, Inc., Miami, Fla.), then mixed with 1 ml of a first lytic reagent composition to lyse red blood cells in a WBC bath. The first lytic reagent contained 25.0 g/L of tetradecyltrimethylammonium bromide, 15.0 g/L of Igepal SS-837 (an ethoxylated phenol from RhOne-Poulenc), 4.0 g/L of Plurofac A38 prill surfactant (from BASF Corp.), and had a pH of 6.2. The experimental hematology analyzer was a modified LH750 (product of Beckman Coulter, Inc., Miami, Fla.), which was equipped with non-focused apertures of a length of 100$\mu$ and a width of 80$\mu$ for measuring the prepared sample mixture as described above. The sample mixture was drawn through a set of three apertures (arranged in parallel) by a constant vacuum. The nucleated blood cells were counted by a DC impedance measurement, and a histogram of the blood cells, after pulse editing, was also produced (averaged from the measurements of three apertures). FIG. 1A shows the obtained DC histogram. As shown for a normal blood sample, the white blood cells had a bi-module distribution, with the lymphoid subpopulation on the left and the myeloid subpopulation on the right. No cell population located on the right side of the myeloid subpopulations.

A second aliquot of 31 $\mu$l of the whole blood sample was mixed with a second lytic reagent in a mixing chamber to lyse the red blood cells, and subsequently mixed with a volume of StabiLyse™ (products of Beckman Coulter, Inc., Miami, Fla.) to retard further lytic reaction in this second sample mixture. The second sample mixture was delivered to a focused flow cell with a sheath fluid, Coulter® LH Series Diluent. The second lytic reagent contained 20 g/L of ethoxylated stearyl amine with 27 moles of ethylene oxide, 1.6 ml of formic acid, and 14 g/L of solubilizer. The second lytic reagent and its use for differentiation of white blood cells are described in U.S. Pat. No. 5,843,608, which is hereby incorporated by reference in its entirety.

The second sample mixture was measured in a focused flow cell by a detector which included a DC measurement means, a radio frequency impedance (RF) measurement means, and a light scatter measurement (LS) means. The light scatter measurement means detects median angle light scatter signals from about 10° to about 70°. A three dimensional scattergram was obtained using the three measured parameters and the functions of these parameter, which was herein referred to as VCS scattergram. FIG. 1B shows the obtained VSC scattergram of the second aliquot of the blood sample. As shown for a normal blood sample, the white blood cells are differentiated into four subpopulations, i.e., monocytes (MO), lymphocytes (LY), neutrophils (NE) and eosinophils (EO) in this two-dimensional (DC vs RLS scattergram). No cell population located in the area above the neutrophils.

FIG. 2A shows a DC histogram of a clinical sample containing immature granulocytes analyzed according to the procedure described above. The manual reference reported about 24% of immature granulocytes (IG), including metamyelocytes, myelocytes and promyelocytes. As shown, there were substantial amount of cells located on the right side of the myeloid subpopulation. FIG. 2B shows a VCS scattergram of the same clinical blood sample shown in FIG. 2A, analyzed according to the procedure described above. As shown, there were substantial amount of cells located in the area above the neutrophils.

EXAMPLE 2

For the purpose of identifying distribution characteristics of immature granulocytes under the process and detection conditions described in Example 1, two types of immature granulocytes were grown in vitro by cell lines.

The first type of immature granulocytes is human promyelocytes grown by HL-60 promyelocytic cell line (ATCC certified cell line CCL-240, HL-60). The second type of immature granulocytes is human promyeloblasts grown by KG-1a cell line (ATCC certified cell line CCL-246.1 KG-1a). The cell culture condition used is known common procedures for cell growth. More specifically, the culture medium used is RPMI 1640 (a product of Roswell Park Memorial Institute, Buffalo, N.Y.), which comprises 10% fetal calf serum, 1% L-glutamine, and 1% penicillin/streptomycin. 50 ml of RPMI 1640 culture medium and 50 ml of a specific type of cells described above were added together and maintained for 24 hours at 37° C. under 5% $CO_2$. The cell concentration upon propagation was determined by counting on a Vi-CELL™ analyzer (a product of Beckman Coulter, Inc., Fullerton, Calif.).

A first test blood sample was prepared by adding $25 \times 10^6$ cells of the promyelocytes described above into 2000 $\mu$L of the normal whole blood sample shown in FIGS. 1A and 1B. The prepared test sample contained about 304 promyelocytes per 100 white blood cells. This level of immature cells is beyond the level of immature granulocytes commonly seen in clinical environment. The high concentration was used for the purpose of identification. The prepared test sample was analyzed according to the procedure described in Example 1. FIG. 3A is the obtained DC histogram of the first aliquot of the prepared test sample, which shows promyelocytes on the right side of myeloid population, which is consistent with the distribution pattern of the immature granulocytes of the clinical whole blood sample. FIG. 3B shows a VCS scattergram from the second aliquot of the prepared test sample, which shows the promyelocytes above the monocytes and granulocytes.

A second test blood sample was prepared by adding $25 \times 10^6$ cells of the promyeloblasts described above into 2000 $\mu$L of the normal whole blood sample shown in FIGS. 1A and 1B. The prepared test sample contained about 304 promyeloblasts per 100 white blood cells. Again, the high concentration was used for the purpose of identification. The second prepared test sample was analyzed according to the procedure described in Example 1. FIG. 3A is the obtained DC histogram of the first aliquot of the second prepared test sample, which showed promyeloblasts on the right side of myeloid population, which was consistent with the distribution pattern of the immature granulocytes of the clinical whole blood sample. FIG. 3B is a VCS scattergram from the second aliquot of the second prepared test sample, which showed the promyeloblasts above the monocytes.

EXAMPLE 3

A clinical sample containing both immature granulocytes and nucleated red blood cells was analyzed according to the procedure described in Example 1. The manual reference reported about 10% of NRBC and about 10% of immature granulocytes, including metamyelocytes, myelocytes and promyelocytes. FIG. 5A is the obtained DC histogram of the first aliquot of the clinical sample, which shows both the NRBC population and the immature granulocytes. FIG. 5B shows a VCS scattergram from the second aliquot of the same clinical blood sample, which shows the NRBC population and the immature granulocytes, directly correlated to cell population distribution of the DC histogram from the first aliquot blood.

The NRBC population was differentiated from the white blood cells, and the ratio between the NRBCs and white blood cells (×100) was reported as the numbers of NRBC/100 WBC. Alternatively, the NRBC can also be reported as absolute count in the blood sample by incorporating the total count of white blood cells.

What is claimed is:

1. A method of measuring immature granulocytes in a blood sample comprising steps of:
   (a) mixing said blood sample with a lytic reagent to lyse red blood cells, and to form a blood sample mixture;
   (b) analyzing said blood sample mixture by a DC impedance measurement, and obtaining a blood cell distribution of said blood sample mixture from said DC impedance measurement;
   (c) determining immature granulocytes only from said blood cell distribution obtained from said DC impedance measurement; and
   (d) reporting immature granulocytes in said blood sample.

2. The method of claim 1 wherein said immature granulocytes comprise myelocytes, promyelocytes, metamyelocytes, myeloblasts and promyeloblasts.

3. The method of claim 1 wherein said analyzing said blood sample mixture by a DC impedance measurement is performed using a non-focused flow aperture.

4. The method of claim 1 wherein said analyzing said blood sample mixture by a DC impedance measurement is performed using a focused flow cell.

5. The method of claim 1 wherein said mixing a blood sample with a lytic reagent comprises diluting said blood sample with a blood diluent to form a diluted blood sample, and mixing said diluted blood sample with said lytic reagent.

6. The method of claim 1 wherein said mixing a blood sample with a lytic reagent comprises mixing said blood sample with a lytic reagent containing a salt to simultaneously dilute and lyse said blood sample.

7. A method of concurrently measuring immature granulocytes and nucleated red blood cells in a blood sample comprising the steps of:
   (a) mixing said blood sample with a lytic reagent to lyse red blood cells, and to form a blood sample mixture;
   (b) analyzing said blood sample mixture by a DC impedance measurement, and obtaining a blood cell distribution from said DC impedance measurement;
   (c) determining nucleated red blood cells and immature granulocytes only from said blood cell distribution obtained from said DC impedance measurement; and
   (d) reporting nucleated red blood cells and immature granulocytes in said blood sample.

8. The method of claim 7 wherein analyzing said blood sample mixture is performed using a non-focused flow aperture.

9. The method of claim 8 wherein said non-focused flow aperture has an aperture aspect ratio of length versus width of 0.7 and greater.

10. The method of claim 9 wherein said non-focused flow aperture has an aperture aspect ratio of length versus width of 1.0 and greater.

11. The method of claim 7 wherein said immature granulocytes comprise myelocytes, promyelocytes, metamyelocytes, myeloblasts and promyeloblasts.

* * * * *